(12) United States Patent
Ouchi et al.

(10) Patent No.: US 8,066,959 B2
(45) Date of Patent: Nov. 29, 2011

(54) AUTOMATIC ANALYZER

(75) Inventors: Katsumi Ouchi, Higashimurayama (JP); Hiroshi Mitsumaki, Tokyo (JP)

(73) Assignee: Hitachi Chemical Company, Ltd., Tokyo (JP)

( * ) Notice: Subject to any disclaimer, the term of this patent is extended or adjusted under 35 U.S.C. 154(b) by 866 days.

(21) Appl. No.: 11/132,301

(22) Filed: May 19, 2005

(65) Prior Publication Data

US 2006/0177344 A1 Aug. 10, 2006

(30) Foreign Application Priority Data

Feb. 9, 2005 (JP) .................. 2005-033257

(51) Int. Cl.
*G01N 35/00* (2006.01)
*G01N 1/00* (2006.01)
(52) U.S. Cl. ......... 422/509; 422/501; 422/68.1; 422/67; 422/50; 700/266; 436/47; 436/43; 436/50; 436/55
(58) Field of Classification Search ............ 422/64, 422/62, 65, 67, 68.1, 104, 50, 63, 100, 500, 422/501, 509; 436/47; 700/266
See application file for complete search history.

(56) References Cited

U.S. PATENT DOCUMENTS

| | | | |
|---|---|---|---|
| 5,230,863 A * | 7/1993 | Salpeter | 422/67 |
| 5,468,453 A * | 11/1995 | Holt et al. | 422/100 |
| 6,270,726 B1 | 8/2001 | Tyberg et al. | |
| 6,375,898 B1 | 4/2002 | Ulrich | |

FOREIGN PATENT DOCUMENTS

AU 199930290 B2 9/1999

(Continued)

OTHER PUBLICATIONS

EP Search Report of Appl. 10 01 2303 dated Dec. 20, 2010 in English.

*Primary Examiner* — Jill Warden
*Assistant Examiner* — Cedric Chan
(74) *Attorney, Agent, or Firm* — Antonelli, Terry, Stout & Kraus, LLP.

(57) ABSTRACT

An automatic analyzer capable of performing analysis in terms of a number of analysis items with high reliability through a simple operation. The automatic analyzer comprises a probe adapted to be moved on a circular arc path and capable of sucking or discharging a sample or reagent, a plurality of sample containers disposed at different positions on the path of the probe and containing different analyte samples, and a rotor capable of carrying a plurality of reagent cartridges. Each of the reagent cartridges comprises a photometric cuvette that is empty when not in use, and a reagent cuvette in which a reagent used for a particular analysis item is hermetically sealed. A two-dimensional code with information regarding the analyte type and analysis conditions, for example, is affixed to the reagent cartridge. The two-dimensional code information is read by a reading unit. Based on the information read from the reagent cartridge, a control unit identifies the sample container in which a analyte sample required by a particular reagent cartridge is contained, and causes the probe to be moved to that sample container. The sample in the sample container is sucked and then discharged into the photometric cuvette of the reagent cartridge. The control unit also causes the probe to suck the reagent in the reagent cuvette of the reagent cartridge and then causes the reagent to be discharged into the photometric cuvette.

13 Claims, 9 Drawing Sheets

FOREIGN PATENT DOCUMENTS

| | | |
|---|---|---|
| DE | 43 12 093 A1 | 10/1993 |
| EP | 0 223 002 A2 | 5/1987 |
| EP | 445616 A2 * | 9/1991 |
| EP | 0 637 750 | 2/1995 |
| JP | 03-065654 | 3/1991 |
| JP | 04-005569 | 1/1992 |
| JP | 05-002616 | 1/1993 |
| JP | 05-232123 | 9/1993 |
| JP | 5-288756 | 11/1993 |
| JP | 07-151766 | 6/1995 |
| JP | 8-262029 | 11/1996 |
| JP | 2000-258430 | 9/2000 |
| JP | 2002-503346 | 1/2002 |
| JP | 2002 258430 | 9/2002 |
| JP | 2004-279432 | 10/2004 |
| WO | WO 95/08774 | 3/1995 |
| WO | WO 99/42841 | 8/1999 |
| WO | WO 99/42921 | 8/1999 |

* cited by examiner

AUTOMATIC ANALYZER

CLAIM OF PRIORITY

The present application claims priority from Japanese application JP 2005-033257 filed on Feb. 9, 2005, the content of which is hereby incorporated by reference into this application.

BACKGROUND OF THE INVENTION

1. Field of Invention

The invention relates to an automatic analyzer capable of automatically analyzing a analyte taken from a subject in terms of a plurality of items.

2. Related Art

An automatic analyzer can be used to analyze a analyte, such as blood or urine, taken from a patient to provide data for the doctor's diagnosis. An example is disclosed in JP Patent Publication (Kokai) No. 5-232123 A (1993), whereby a plurality of types of samples from a single patient that are set on a rack with a patient ID number are measured. A plurality of items of measurement data are then combined and subjected to a logic check to distinguish equipment abnormality from patient abnormality. Another example is disclosed in JP Patent Publication (Kokai) No. 2000-258430 A, whereby a plurality of analytes with individual sample IDs are carried on a sample rack with a rack ID. Based on the reading of the sample ID or the rack ID, each rack is transported to an analysis module corresponding to a requested analysis item. In the analysis module, the analyte sample and a reagent are dispensed into a reaction vessel for measurement. In yet another example of the automatic analyzer, JP Patent Publication (Kohyo) No. 2002-503346 A discloses an analysis system employing a system reagent carrier containing a plurality of chambers or cuvettes.

Patent Document 1: JP Patent Publication (Kokai) No. 5-232123 A (1993)

Patent Document 2: JP Patent Publication (Kokai) No. 2000-258430 A

Patent Document 3: JP Patent Publication (Kohyo) No. 2002-503346 A

SUMMARY OF THE INVENTION

In the automatic analyzer disclosed in JP Patent Publication (Kokai) No. 5-232123 A (1993), as many reagents as there are analysis items must be prepared in a cooler because a prepared reagent must be transferred to a reaction disc by a dispenser where it is mixed with a sample set on the disc for analysis. Thus, if analysis needs to be performed in a number of items, a large-sized cooler would be required, making the system larger in size. The automatic analyzer disclosed in JP Patent Publication (Kokai) No. 2000-258430 A is not adapted to the analysis of a plurality of items of a plurality of kinds of analytes taken from an individual patient. Although JP Patent Publication (Kohyo) No. 2002-503346 A discloses the system reagent carrier containing a plurality of chambers or cuvettes, the publication does not describe the details of the analysis method utilizing the system reagent carrier.

It is therefore an object of the invention to provide an automatic analyzer capable of performing analysis in terms of a number of analysis items in a highly reliable manner with simple operations.

An automatic analyzer of the invention comprises a probe adapted to be moved along a circular arc path for sucking and discharging a sample or reagent, a plurality of sample containers disposed on the path of movement of the probe for storing different analyte samples, and a rotor capable of carrying and rotating a plurality of reagent cartridges for different analysis items. Each of the reagent cartridges comprises a photometric cuvette that is empty when not in use, and a reagent cuvette in which a reagent used for a particular analysis item is hermetically sealed. A two-dimensional code containing information regarding the type of analyte to be analyzed by a particular reagent cartridge and analysis conditions, for example, is affixed to each reagent cartridge. The information in the two-dimensional code affixed to each reagent cartridge is read by causing the reagent cartridge to pass by a fixed reading unit by rotating the rotor. The information thus read is stored in a memory unit.

Based on the information read from the reagent cartridges, the control unit identifies the sample container in which a analyte sample required by each reagent cartridge is stored, and causes the probe to be moved to the sample container where the sample is sucked. The control unit then causes the probe to be moved above the rotor and causes the sucked sample to be discharged into the photometric cuvette of the reagent cartridge. The control unit also causes the probe to suck a reagent in the reagent cuvette of the reagent cartridge and then causes the reagent to be discharged into the photometric cuvette. The sucking and discharging of the sample and reagent are performed by the single probe while controlling the position of the probe and that of the reagent cuvette relative to the probe in a synchronized manner. When the measurement of the sample mixed with the reagent in the photometric cuvette is performed, the reagent cartridge is positioned on the optical path of the optical measurement unit by rotating the rotor.

In accordance with the invention, the sucking and discharging of the sample and reagent can be performed by simply controlling the rotational position and the lifting and lowering of a single probe, and the rotation of the rotor on which the reagent cartridges are carried. Thus, the drive mechanism can be simplified and reduced in size. Furthermore, an automatic analysis can be performed by simply setting necessary analytes on the device and setting reagent cartridges corresponding to required analysis items on the rotor. Thus, the analysis procedure can be simplified and the chances of failure due to erroneous operation of the apparatus or the like can be eliminated.

DESCRIPTION OF THE PREFERRED EMBODIMENTS

Embodiments of the automatic analyzer according to the invention will be described with reference to the drawings.

Figure 1:
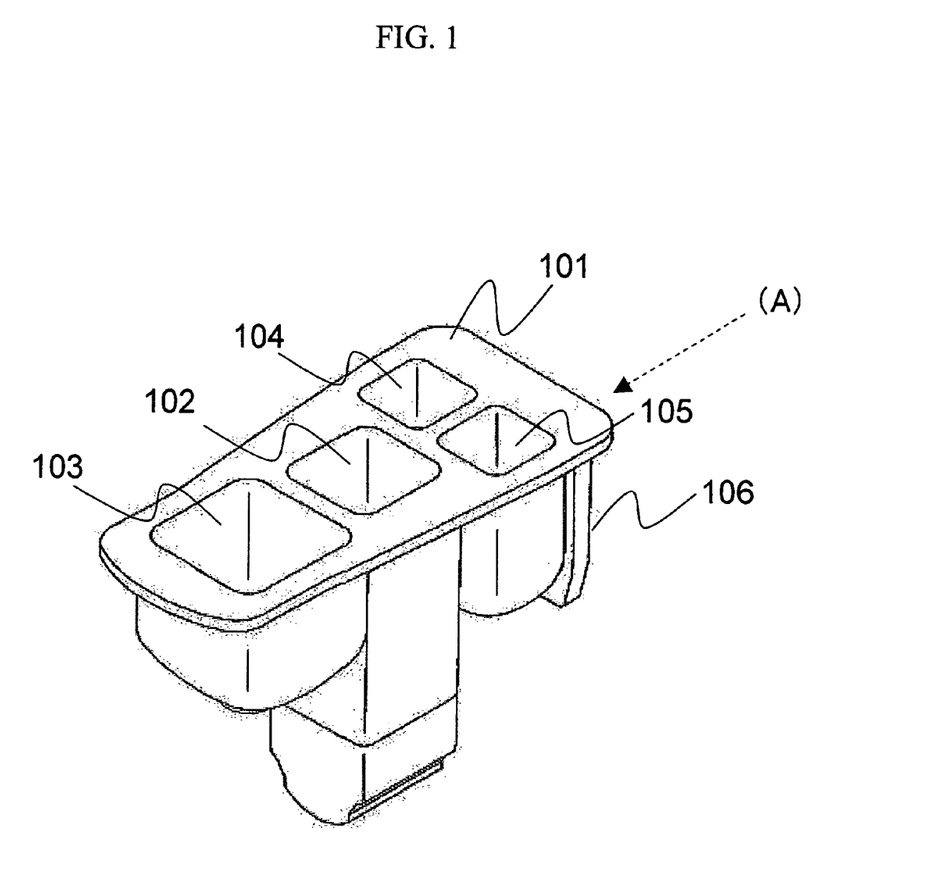
FIG. 1 shows a perspective view of an example of a reagent cartridge.
Figure 2:
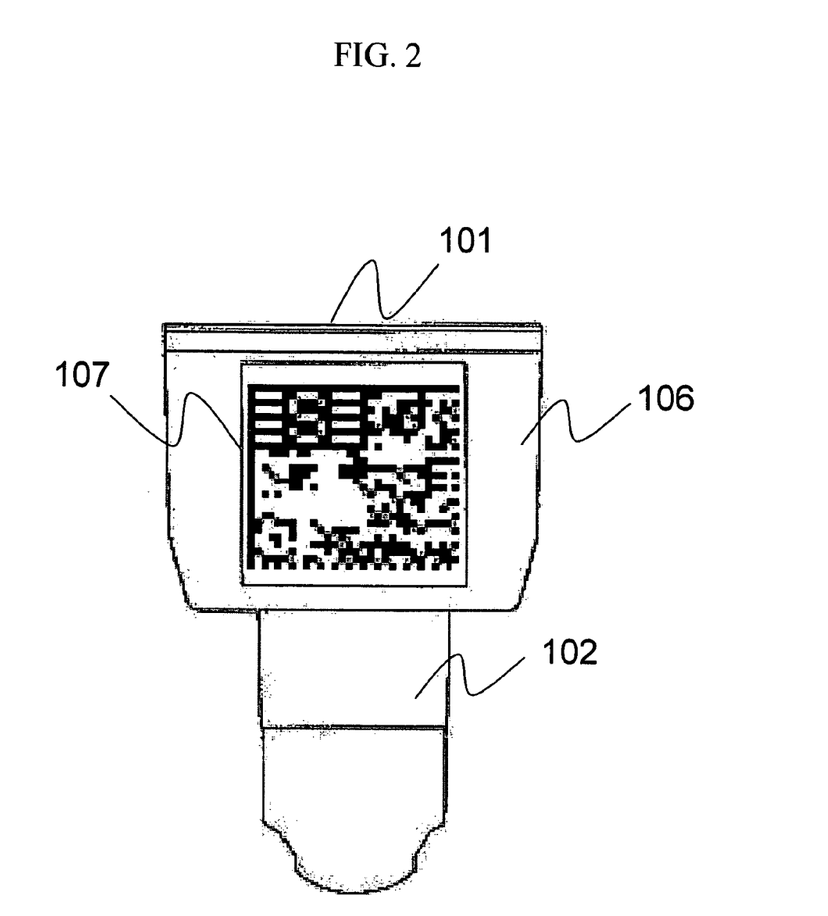
FIG. 2 shows a side view of the reagent cartridge.

FIG. 1 shows a perspective view of an example of a reagent cartridge used in the automatic analyzer of the invention. FIG. 2 shows a side view of the reagent cartridge seen from the direction of (A) in FIG. 1.

A reagent cartridge 101 is made of polypropylene, for example. It includes one photometric cuvette 102 and three reagent cuvettes, namely, a first reagent cuvette 103, a second reagent cuvette 104, and a third reagent cuvette 105, in the illustrated example. Although the reagent cartridge 101 of the present embodiment includes the first to third cuvettes, the second and third cuvettes may be combined into a single second cuvette in another embodiment. The photometric cuvette 102 is empty prior to analysis. After it is injected with a sample and reagents by the automatic analyzer and the mixture is stirred, analysis is performed in the photometry section.

In a case where one kind of reagent is necessary for analysis, the first and second reagent cuvettes 103 and 104 are loaded with the same reagent. In a case where two kinds of reagents are necessary, the first reagent cuvette 103 and the second reagent cuvette 104 are loaded with individual reagents. When three kinds of reagents are necessary, the first reagent cuvette 103, the second reagent cuvette 104, and the third reagent cuvette 105 are loaded with individual reagents.

In the reagent cartridge 101, reagents necessary for the examination items for the reagent cartridge are put in the individual reagent cuvettes in advance, with the photometric cuvette 102 remaining empty, and the cartridge is closed with its entire top surface hermetically sealed. The seal is printed with the test items that can be examined on the reagent cartridge, such as "TP" for a reagent cartridge for total protein analysis, or "UA" for a reagent cartridge for uric acid analysis. The seal is further marked with different colors corresponding to the type of analytes necessary for analysis, such as yellow for a reagent cartridge involving a blood serum sample; green for a reagent cartridge involving a urine sample; red for a reagent cartridge involving a whole blood sample; or blue for a reagent cartridge requiring other samples. The color-coding scheme facilitates the user's preparation of necessary analyte samples for analysis.

At the rear of the reagent cartridge, there is a panel 106 affixed with a seal 107 printed with a dot code (two-dimensional code) as shown in FIG. 2, for example. The dot-code seal 107 contains the following information encoded at certain positions: (1) date of manufacture and expiration date; (2) serial number; (3) analyte type required as a sample; (4) required amount of sample and dispensing timing; (5) required amount of a first reagent and dispensing timing (6) required amount of a second reagent and dispensing timing; (7) required amount of a third reagent and dispensing timing; (8) photometry method; (9) timing of photometry; (10) main/sub wavelength for photometry; and (11) formula for conversion of absorbance into concentration. These pieces of information are read by a dot-code reader inside the automatic analyzer and then stored in a RAM, also inside the automatic analyzer.

The reagent cartridge 101 with a hermetically sealed top surface is stored in a cooler prior to analysis. The reagent cartridge is disposable, and at the end of analysis, the user can remove the cartridge with the solutions inside it from the automatic analyzer and dispose of it.

Figure 3:
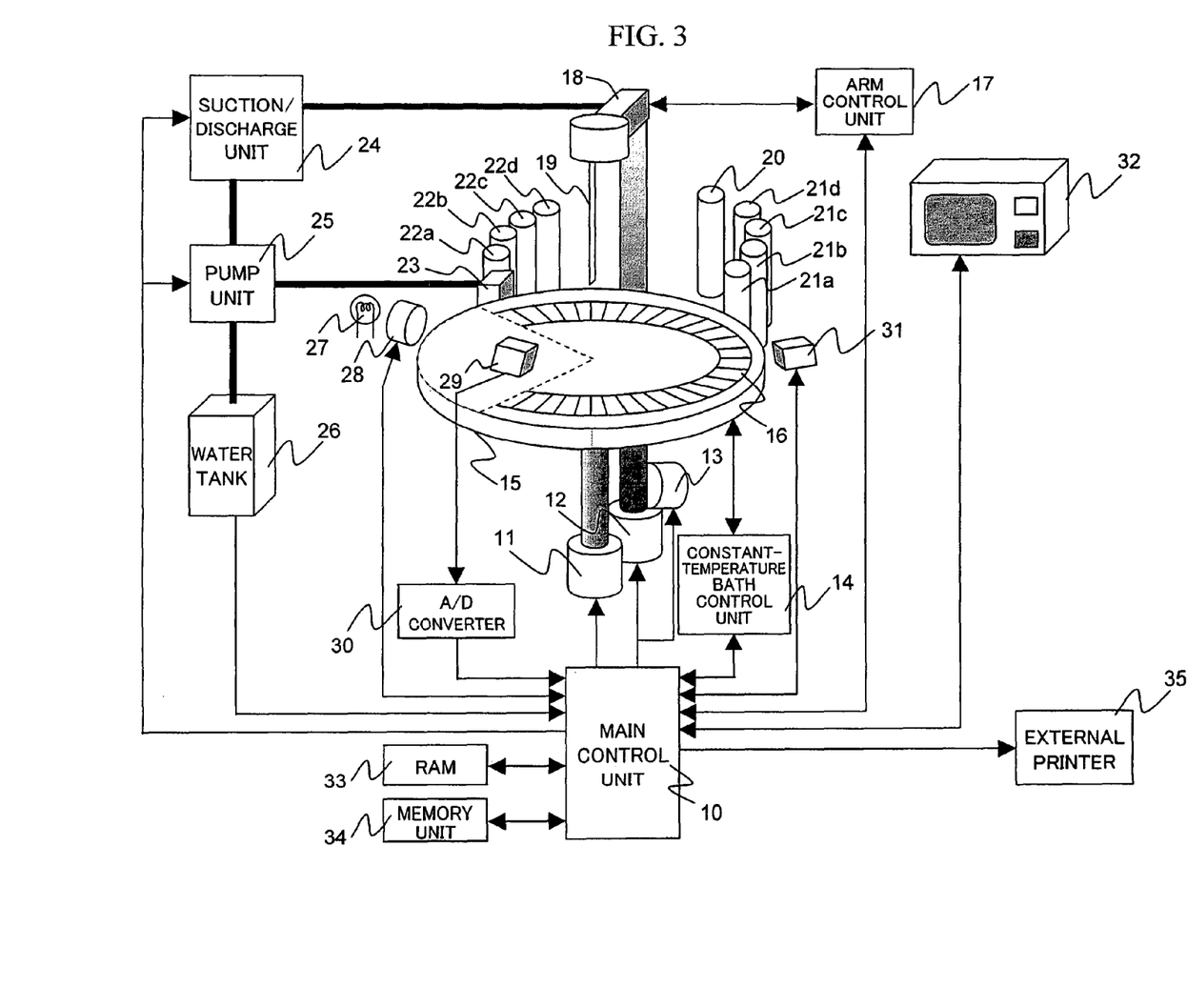
FIG. 3 shows a schematic view of an example of the overall structure of an automatic analyzer according to the invention.
Figure 4:
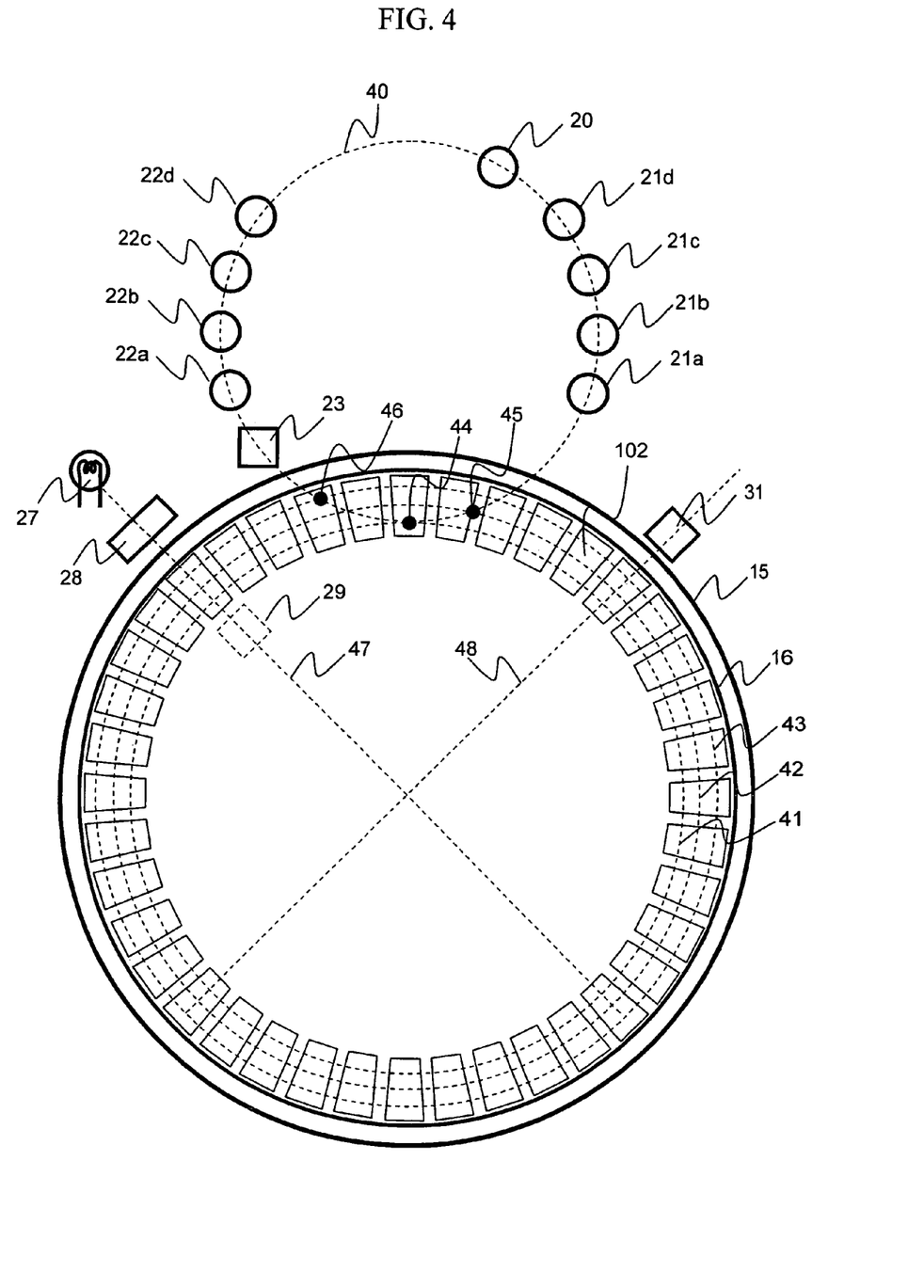
FIG. 4 shows a schematic plan view of the automatic analyzer of the invention.

With reference to FIGS. 3 and 4, the automatic analyzer of the invention is described. FIG. 3 schematically shows an overview of an example of the automatic analyzer of the invention. FIG. 4 schematically shows a plan view.

The automatic analyzer is connected to commercial power supply and can be turned on via a power switch (not shown).

The overall operation of the automatic analyzer is controlled by a main control unit 10, which mainly consists of a CPU, a ROM, and a real-time clock. A RAM 33 is also connected as a temporary memory to be referenced by the main control unit 10.

A rotor 16 as a carrier for the reagent cartridge 101 is disposed inside a constant-temperature bath 15. The constant-temperature bath 15 is fitted with a heater so that the temperature of air inside can be controlled to be 37° C. by a constant-temperature bath control unit 14. The rotor 16, which can be rotated by controlling a step motor 11, is capable of mounting a maximum of 40 reagent cartridges in the circumferential direction. The individual reagent cartridges are installed on the rotor 16 such that their rear panels 106 affixed with the dot-code seals 107 face the periphery of the rotor.

An arm 18 can be moved up and down by a vertical movement-controlling step motor 13. It can also be rotated in a horizontal plane by a rotation controlling step motor 12. At the end of the arm 18, a probe 19 is attached that extends vertically downward. The probe 19 is mainly used for the suction and discharge of samples and cleaning solution. The probe 19 has a sharp tip like that of an injection needle, so that it can penetrate the hermetic seal of the photometric cuvette 102 and the individual reagent cuvettes 103,104, and 105 of the reagent cartridge 101. A heater (not shown) is fitted to the probe 19 in order to maintain the temperature of the probe at 37° C. by an arm control unit 17. The probe 19 is additionally used for detecting the fluid level. Specifically, the change in the capacitance between the probe 19 and ground potential is detected using the arm control unit 17. This function is used for checking the volume of the sample and cleaning solution. As the fluid level of the sample or cleaning solution is detected by the arm control unit 10 during the descent of the probe 19, a detection signal is sent to the main control unit 10. Numeral 20 designates a housing as the home position of the probe 19.

Numerals 21a to 21d designate sample containers that are disposed along a circumference 40 with the radius corresponding to the distance between the rotation axis of the arm and the probe 19. Each of the sample containers 21a to 21d is assigned position information for identification by the main control unit 10, and the position information regarding a particular container with a sample required by the reagent cartridge contained in it is stored in the dot code. The sample containers 21a to 21d are marked with the same colors as those of the seal of the reagent cartridges, indicating the required analyte types. For example, the sample container 21a is for blood serum or blood plasma and is therefore marked with yellow. The sample container 22b is for a whole blood sample and is therefore marked with red. The sample container 22c is for a urine sample and is therefore marked with green. The sample container 22d is for other sample types and is therefore marked with blue. The individual sample containers 21a to 21d are removable from the automatic analyzer.

Numerals 22a to 22d designate cleaning solution containers, which are disposed along the circumference 40 with the radius corresponding to the distance between the arm rotation axis and the probe 19. The cleaning solution containers 22a to 22d are likewise color-marked in a manner corresponding to the cleaning solutions. For example, the container 22a is an alkaline cleaning solution container and is marked with blue. The container 22b is an acidic cleaning solution and is marked with yellow. The container 22c is a neutral cleaning solution container and is marked with red. The container 22d is a reserve container and is not color-marked. The individual cleaning solution containers 22a to 22d can be removed from the automatic analyzer.

Numeral 44 designates a aspiration site for a first reagent. It is located at the point of contact between a circumference 41 that passes through the center of the first reagent cuvette of each reagent cartridge and the circumference 40 with the radius corresponding to the distance between the arm rotation axis and the probe 19. When the first reagent in the first reagent cuvette of the reagent cartridge is sucked by the probe 19, the rotor 16 is rotated prior to suction so as to position the center of the first reagent cuvette of the reagent cartridge of interest at the aspiration site 44.

Numeral 45 designates a aspiration/discharge site for the photometric cuvette 102 of the reagent cartridge 101. It is located at the point of contact between a circumference 42 that passes through the center of the photometric cuvette 102 of each reagent cartridge, and the circumference 40 with the radius corresponding to the distance between the arm rotation axis and the probe 19. When a sample or a reagent is discharged or sucked into or out of the photometric cuvette 102 of the reagent cartridge 101, the rotor 16 is rotated prior to suction or discharge so as to position the center of the photometric cuvette 102 of the reagent cartridge 101 of interest at the aspiration/discharge site 45.

Numeral 46 designates a aspiration site for the second and third reagents. It is located at the point of contact between a circumference 43 that passes through the center of the second and third reagent cuvettes 104 and 105 of the reagent cartridge 101, and the circumference 40 with the radius corresponding to the distance between the arm rotation axis to the probe 19. When the second reagent in the second reagent cuvette of the reagent cartridge is sucked by the probe 19, the rotor 16 is rotated prior to suction so as to position the center of the second reagent cuvette 104 of the reagent cartridge of interest at the aspiration site 46. When sucking the third reagent in the third reagent cuvette of the reagent cartridge by the probe 19, the rotor 16 is rotated prior to suction so as to bring the center of the third reagent cuvette 105 of the reagent cartridge of interest to be at the aspiration site 46.

The constant-temperature bath 15, rotor 16, arm 18, probe 19, housing 20, sample containers 21a to 21d, and cleaning solution containers 22a to 22d are covered with an openable and closable lid (not shown). Near the lid, a lid opening detection switch and a lid locking mechanism (not shown) are attached. When the lid is open, the lid opening detection switch is turned on and a detection signal is sent to the main control unit 10. The lid can also be locked by the lid locking mechanism when activated under the control of the main control unit 10.

A washing station 23 is a site where the inside and outside of the probe 19 are washed. During washing with purified water, purified water is ejected out of the inner walls of the washing station 23 upon activation of a pump unit 25, and the outside of the probe is washed with the purified water. The inside of the probe is washed with purified water that is ejected out of the probe 19 upon activation of a aspiration/discharge unit 24 and pump unit 25. During washing with the cleaning solutions, the cleaning solution that has been sucked from any of the cleaning solution containers 22a to 22d by the probe 19 is discharged inside the washing station. The waste liquid after washing is discharged to the outside of the automatic analyzer.

The aspiration/discharge unit 24 sucks or discharges a sample, a reagent, cleaning solution, or the like under the control of the main control unit 10. It also washes the inside and outside of the probe 19 with purified water in association with the pump unit 25. A water tank 26, which stores the purified water necessary for the probe washing, is fitted with a level reduction-detecting switch (not shown). When the volume of the purified water drops below a predetermined level, the level reduction-detecting switch sends a detection signal to the main control unit 10.

A light source unit 27, optical system unit 28, and photodetector unit 29 are constituent elements of a spectrophotometer, and they are used for performing an absorbance measurement on the photometric cuvette of the reagent cartridge. The light source unit 27 includes a tungsten lamp, which is constantly turned on as long as the automatic analyzer is on.

The optical system unit 28 includes a rotating wavelength selection filter, lenses, and a slit. The rotating wavelength selection filter can be rotated under the control of the main control unit 10 so as to position a desired filter on an optical axis 47. The wavelengths that can be selected by the rotating wavelength selection filter are 340 nm, 380 nm, 415 nm, 450 nm, 480 nm, 508 nm, 546 nm, 576 nm, 600 nm, 660 nm, 700 nm, and 800 nm, for example.

The photodetector unit 29 includes a photodiode and an amplifier. It is disposed on the optical axis 47 below the rotor 16. The amount of light detected by the photodiode is fed to the amplifier in the form of a voltage and amplified therein. The amplified analog voltage value is converted into digital data by an A/D converter 30 and the data is fed to the main control unit 10.

Numeral 31 designates a dot-code reader. It optically reads the dot code affixed to the panel 106 of the reagent cartridge over the optical axis 48. The thus read data is transmitted to the main control unit 10.

Numeral 32 designates a display/operating unit that includes a touch-sensitive panel LCD, a START button, and a STOP button. The touch-sensitive panel LCD allows the user to select a particular process by pressing a predetermined position on the panel, as well as displaying messages or analysis results to the user. The START button is used for initiating an analysis operation. The STOP button is used for interrupting the analysis operation.

Numeral 34 designates a memory unit for storing the analysis result together with the patient ID and the date and time of analysis. In the memory unit 34, past analysis results can be stored.

Numeral 35 designates an external printer connected to the automatic analyzer via a standard interface. The external printer 35, which is optional, is used for printing the analysis result.

Figure 5:
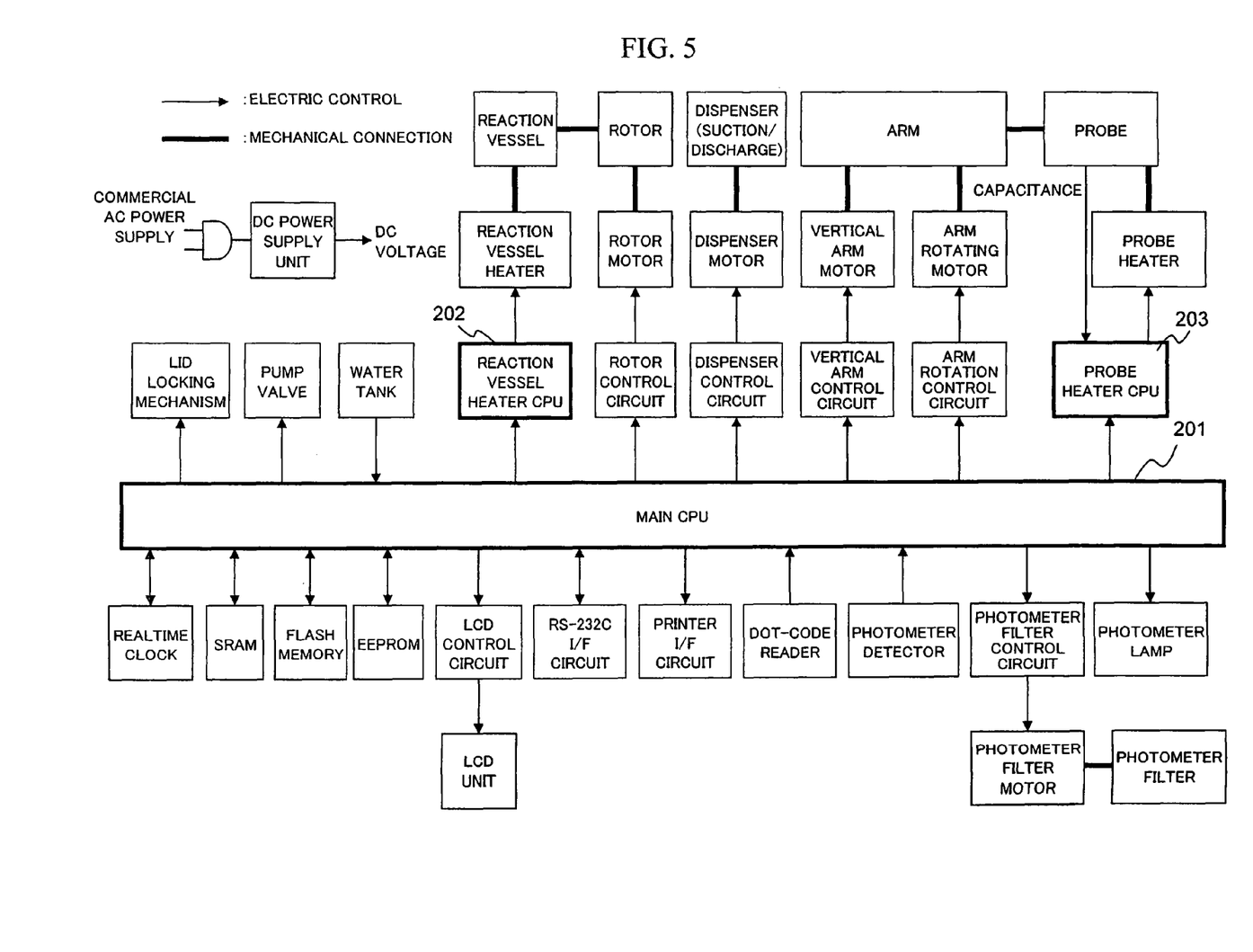
FIG. 5 shows a block diagram of a control system of the automatic analyzer.

FIG. 5 is a block diagram of the control system of the automatic analyzer shown in FIGS. 3 and 4. A main CPU 201 is provided in the main control unit 10. A CPU 202 for a reaction bath heater is provided in the constant-temperature bath control unit 14. A CPU 203 for a probe heater is provided in the arm control unit 17.

Figure 6:
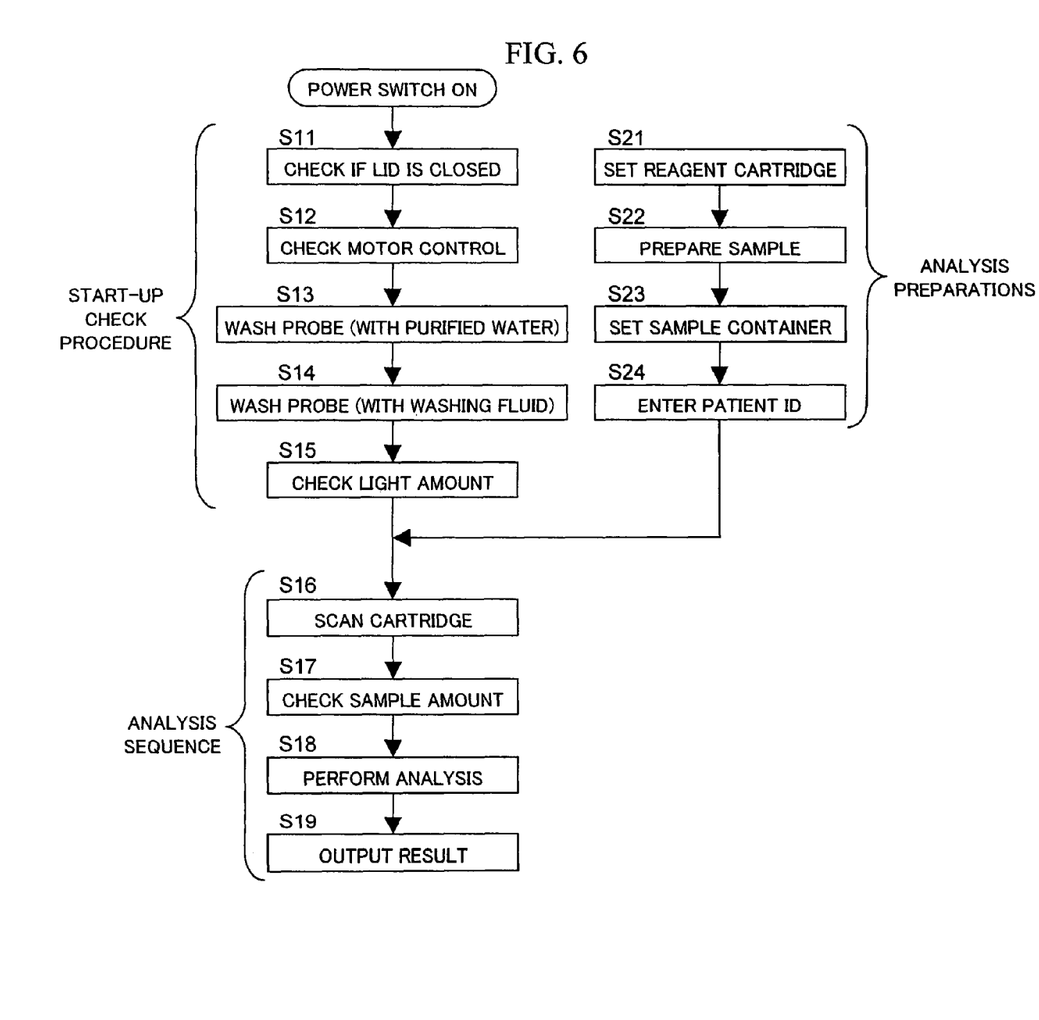
FIG. 6 shows an operational flowchart of the automatic analyzer of the invention.

With reference to FIG. 6, the operation flow of the automatic analyzer of the invention is described.

As the power switch is turned on, a start-up check procedure is launched. In this procedure, the main control unit 10 first checks whether the lid is closed, using the lid opening detection switch (S11). If it is confirmed that the lid is closed, the main control unit 10 then controls the lid locking mechanism to lock the lid. Then, the main control unit 10 checks whether or not each step motor can be correctly controlled (S12).

Thereafter, prior to washing the probe 19 with purified water, it is checked if the volume of purified water in the water tank 26 is more than a predetermined level, using the level detection switch. During the washing of the probe 19, the main control unit 10 causes the tip of the probe 19 to be moved into the washing station 23. The main control unit 10 then controls the pump unit 25 such that water is ejected out of the external walls of the washing station 23, with which to wash the outside of the probe 19. At the same time, the main control unit 10 controls the pump unit 25 and the aspiration/discharge unit 24 so as to cause water to be ejected out of the probe 19, thereby washing the inside of the probe 19 (S13).

Thereafter, prior to washing the probe 19 with four kinds of cleaning solutions, the fluid level of each cleaning solution is checked. Specifically, the fluid level is calculated from the height of cleaning solution detected by the probe 19 to determine whether the fluid level is above a predetermined level. A predetermined volume of cleaning solution is then sucked into the probe 19, and the inside of the probe 19 is washed therewith. The probe 19 is then moved to the washing station 23 where the cleaning solution is discharged. The inside and outside of the probe 19 are then washed with purified water at the washing station 23. The above process is performed for each cleaning solution (S14).

Finally, the lamp is turned on to check, using the photodetector, if the amount of light when a 340 nm filter is set on the optical axis is more than a predetermined value (S15).

Thus the start-up check procedure is completed and analysis preparations for the automatic analyzer are made. In the following, analysis preparations made by the user are described.

First, the user picks out a reagent cartridge 101 corresponding to a particular analysis item from the cooler, and sets it on the rotor 16 of the automatic analyzer (S21). The position of the reagent cartridge 101 on the rotor 16 may be arbitrary.

Then, the type of sample required for the patient's analysis (such as blood serum, blood plasma, whole blood, or urine, for example) is determined from the color of the seal of all of the reagent cartridges mounted on the rotor 16, and the sample is injected into a sample container (S22). The sample container is then set on the automatic analyzer (S23). Finally, the user enters the patient ID on the display/analysis unit 32 (S24).

The analysis preparations by the user are thus completed. Analysis can be started by pressing the START button on the display/operating unit. In the following, an analysis sequence will be described.

Initially, the main control unit 10 controls the step motor 11 to rotate the rotor 16 so as to put the reagent cartridges on the optical axis 48 sequentially. The dot code on the reagent cartridges are then read by the dot-code reader 31 (S16). The information in the dot code thus read is stored in RAM 33. Of the dot code information stored in RAM33, if the aforementioned information (2) regarding serial numbers agrees with that of a reagent cartridge that has been used for analysis in the past and stored in the memory unit 34, this shows that the reagent cartridge now disposed on the optical axis 48 has already been used for analysis. In this case, a message is displayed on the display/operating unit 32 requesting the removal of the cartridge, and the analysis process is terminated. Even if the reagent cartridge has not been used for analysis, a similar error message is displayed on the display/operating unit 32 and the analysis process is terminated if it is determined that the expiry date of the reagent cartridge has passed based on the aforementioned information (1) regarding the date of manufacture and the expiry date stored in RAM 33.

When the scanning of the reagent cartridge 101 is completed, the sample required for a single analysis operation can be identified, and the volume of the sample is then checked. Specifically, the probe 19 is moved to the sample container from which the sample is collected for analysis, and the volume of sample is calculated based on the detected height of fluid level of the sample (S17). The probe is then moved to the washing station 23 where it is washed with purified water. At the start of analysis, an absorbance measurement is performed on each reagent cartridge (S18), and the result is outputted to the display/operating unit 32 (S19).

Figure 7:
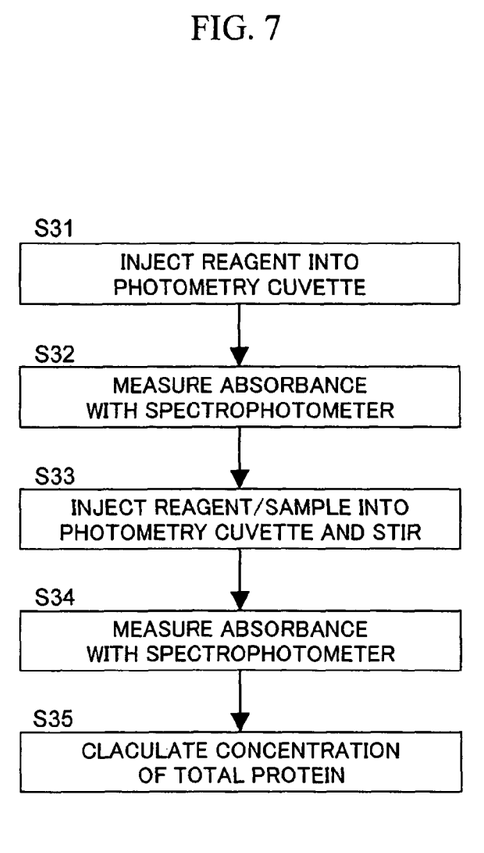
FIG. 7 shows a flowchart of an example of absorbance measurement.
Figure 8:
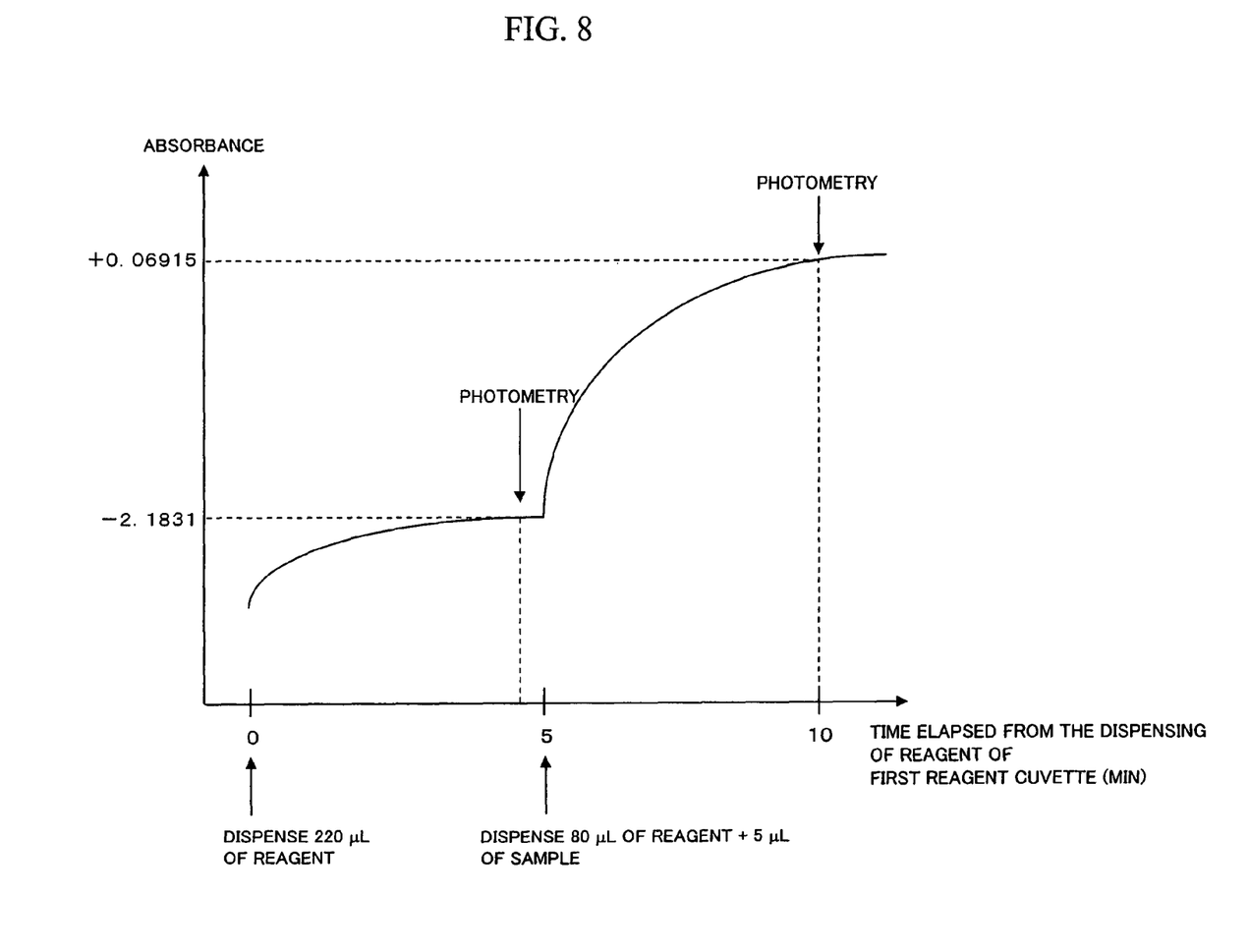
FIG. 8 shows an example of the temporal change in absorbance, the timing of dispensing a reagent/sample, and the timing of photometry.

FIG. 7 shows the flow of absorbance measurement for a reagent cartridge for the analysis of total protein (TP), for example. FIG. 8 shows the temporal changes in absorbance and the timing for the dispensing and photometry of reagent/sample.

The reagent cartridge, which is hermetically sealed prior to analysis, contains 250 µl and 100 µl of the same reagent in the first reagent cuvette and the second reagent cuvette, respectively. Since the reagent cartridge in the present example employs blood serum as a sample, the seal is marked yellow and is printed with the analysis item "TP". The dot code seal affixed to the reagent cartridge contains the aforementioned information regarding the analysis and processing procedures, including: "blood serum or plasma" for information (3) regarding the type of analyte; "5 µl/5 min after the initial dispensing of reagent" for information (4) regarding the required volume of sample and dispensing timing; "220 µl/0 min after the initial dispensing of reagent" for information (5) regarding the required volume of a first reagent and dispensing timing; "80 µl/5 min after the initial dispensing of reagent" for information (6) regarding the required volume of a second reagent and dispensing timing; "2-point end assay" for information (8) regarding the photometry method; "4 min 40 sec/10 min after initial dispensing of reagent" for information (9) regarding photometry timing; "main wavelength 546 nm/sub wavelength 700 µm" for information (10) regarding the main/sub wavelength for photometry; and "concentration=absorbance difference×970.6 g/dl" for information (11) regarding the formula for converting absorbance into concentration.

In accordance with the information read from the dot code seal and stored in RAM 33, the main control unit 10 controls the individual units of the system so as to initially dispense the reagent in the first reagent cuvette into the photometric cuvette (S31). Specifically, the rotor 16 is rotated such that the center of the first reagent cuvette of the reagent cartridge is positioned at the aspiration site 44. The arm 18 is then rotated so as to move the probe 19 to the aspiration site 44. The probe 19 is then lowered such that the tip of the probe can penetrate the seal into the first reagent cuvette. The 220 µl of the reagent is then sucked from the first reagent cuvette. The probe 19 is then lifted and the rotor 16 is rotated so as to bring the center of the photometric cuvette to be at the aspiration/discharge site 45. Thereafter, the arm 18 is rotated to move the probe 19 to the aspiration/discharge site 45, where the probe 19 is lowered. When the probe tip penetrates the seal into the photometric cuvette, the reagent is discharged into the photometric cuvette.

Four minutes and 40 seconds after the initial dispensing of the reagent, the main control unit 10 controls the individual units of the system so as to perform an absorbance measurement on the photometric cuvette with the reagent in it (S32). Specifically, the rotor 16 is rotated such that the center of the photometric cuvette of the reagent cartridge is positioned at the optical axis 47. Thereafter, a photometric measurement is performed using the spectrophotometer consisting of the light source unit 27, optical system unit 28, and photodetector unit 29 at the main/sub wavelengths of 546 nm and 700 nm. The measured absorbance in the example is −0.21831, as shown in FIG. 8.

Five minutes after the initial dispensing of the reagent, the main control unit 10 controls the individual units of the system so as to dispense the reagent in the second reagent cuvette and the sample into the photometric cuvette (S33). Specifically, the rotor 16 is rotated so as to bring the center of the second reagent cuvette of the reagent cartridge at the aspiration site 46. Thereafter, the probe 19 is moved to the aspiration site 46 where the 80μl of reagent is sucked form the second reagent cuvette. The analyte type information stored in RAM33, namely, "blood serum or plasma," in the present example, is then referenced. Because the analyte type and the sample container are associated on a one-to-one basis, the main control unit 10 can identify the sample container 21a with blood serum in it. After the probe 19 is moved to position of the blood serum sample container 21a, 5 μl of blood serum is sucked from the blood serum sample container. The rotor 16 is then rotated such that the center of the photometric cuvette is positioned at the aspiration/discharge site 45. The probe 19 is then moved to the aspiration/discharge site 45, where the reagent and sample are discharged into the photometric cuvette. The mixture of the reagent and sample in the photometric cuvette is then sucked and discharged by the probe 19, thereby stirring the mixture.

Figure 9:
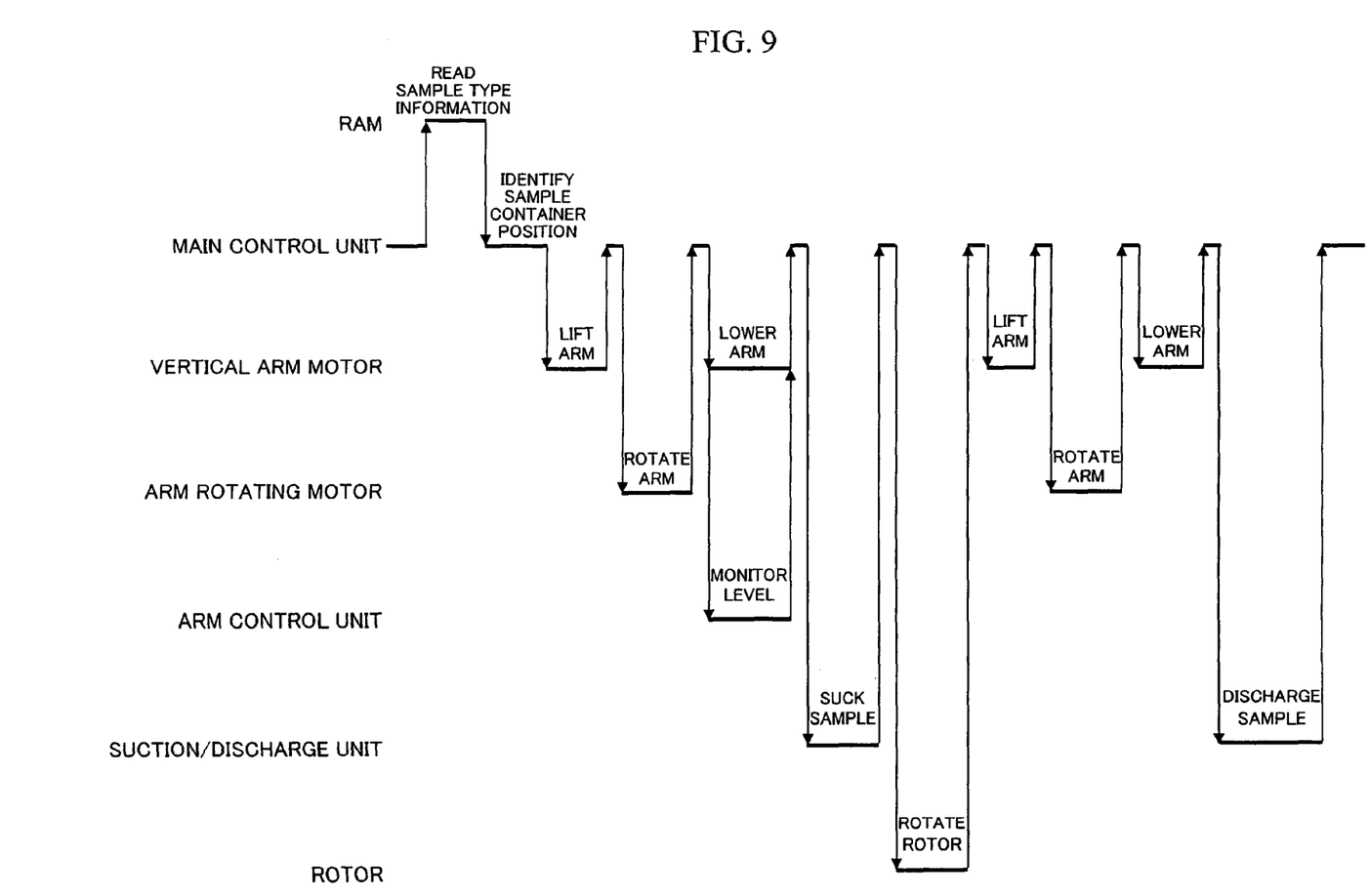
FIG. 9 shows an example of control sequence of the individual units of hardware.

FIG. 9 shows an example of the control sequence of each element of hardware, staring from the referencing of RAM 33 to the discharge of the mixture of reagent and sample. First, the main control unit 10 references RAM 33 to read the analyte type information. Based on the analyte type information, the main control unit 10 identifies the position of the sample container, namely, sample container 21a in the present example. The sequence then moves on to the operation for sucking the sample from the sample container 21a using the probe 19. For this purpose, the main control unit 10 controls the vertical movement step motor 13 so as to lift the arm 18. Then, the rotation control step motor 12 is controlled to rotate the arm 18 by a predetermined angle so that the probe 19 can be positioned above the sample container 21a. Thereafter, the vertical movement step motor 13 is controlled to lower the arm 18. When the tip of the probe 19 enters into the sample in the sample container 21a sufficiently deeply, the lowering movement of the arm 18 is terminated, while the fluid level is being monitored by the arm control unit 17 as it detects the change in capacitance between the probe 19 and ground potential. The main control unit 10 then controls the aspiration/discharge unit 24 so that a predetermined volume of the sample in the sample container 21a can be sucked by the probe 19.

The main control unit 10 then controls the step motor 11 to rotate the rotor 11 such that the center of the photometric cuvette 102 of the reagent cartridge 101 used for analysis is positioned at the aspiration/discharge site 45. The rotational movement of the rotor 11 may be performed simultaneously and in parallel with the operation of the probe 19 sucking sample from the sample container 21a.

On the other hand, the main control unit 10 controls the vertical movement step motor 13 to lift the arm 18, thereby pulling the probe 19 that has sucked the sample out of the sample container 21a. The main control unit 10 then controls the rotation control step motor 12 to turn the arm 18 such that the probe 19 is positioned above the aspiration/discharge site 45. Thereafter, the main control unit 10 controls the vertical movement step motor 13 to lower the arm 18 towards the photometric cuvette 102 of the reagent cartridge 101 and cause the tip of the probe 19 to penetrate the seal into the photometric cuvette 102. Once the tip of the probe 19 is inside the photometric cuvette 102, the lowering of the arm 18 is terminated. The main control unit 10 then controls the aspiration/discharge unit 24 so that the sample that has been sucked into the photometric cuvette 102 can be discharged via the tip of the probe 19.

Referring back to FIG. 7, 10 minutes after the initial dispensing of the reagent, the main control unit 10 controls the individual units of the system to perform an absorbance measurement on the photometric cuvette containing the mixture of the reagent and sample (S34). In this case, the rotor 16 is rotated such that the center of the photometric cuvette of the reagent cartridge is positioned at the optical axis 47. An absorbance measurement is performed using the spectrophotometer consisting of the light source unit 27, optical system unit 28, and photodetector unit 29 at main/sub wavelengths of 546 nm and 700 nm. It is seen from FIG. 9 that the measured absorbance in the present example is =+0.06915.

The difference between the two measurements of absorbance, or +0.06915−(−0.21831)=+0.28746, is substituted into the formula stored in RAM33 for converting absorbance into concentration, i.e., "concentration=absorbance×970.6 g/dl," resulting in the total protein concentration of 6.244153 g/dl (S35).

When the concentration measurement for the analysis item of the initial reagent cartridge is completed, the next and all the rest of the reagent cartridges set on the rotor 11 are measured sequentially for concentration for the analysis item set in each reagent cartridge. Preferably, the order of measurement is determined such that reagent cartridges with the same analyte type are measured at once. For example, when 20 reagent cartridges that employ blood serum as a sample and 10 reagent cartridges that employ urine as a sample are mounted on the automatic analyzer, a concentration measurement is initially performed on the 20 reagent cartridges for blood serum in succession, and then the 10 reagent cartridges for urine are measured for concentration in succession.

The analysis result is displayed on the display/operating unit 32 and also stored in the memory unit 34, together with the patient ID, time and day, and the serial number of the reagent cartridge used. In a case where the external printer 35 is connected, the analysis result is printed out on the printer, and then the entire process is normally completed. In the memory unit 34, past analysis data can be stored, so that specific past analysis data can be selected on the display/operating unit 32 for printout using the external printer at any time.

Thus, by transporting a plurality of analytes arranged at predetermined positions to a particular reagent cartridge using a single probe, in accordance with the dot code information affixed to the reagent cartridge, as in the present embodiment, the multiple analytes can be analyzed in terms of a plurality of analysis items using the automatic analyzer of simple structure including a single probe. In the automatic analyzer of the present embodiment, a sample/reagent discharge site is located at the point of intersection of the circumference of rotation of the probe and that of the photometric cuvette, and the reagent aspiration site is located at the point of intersection of the circumference of rotation of the probe and that of the reagent cuvette. Specimens of different types are contained in separate sample containers arranged at predetermined positions on the circumference of rotation of the probe. The automatic analyzer of the present embodiment further mounts reagent cartridges that require a plurality of types of samples. The automatic analyzer is capable of sampling a required analyte sample without mistaking the sample container based on the analyte type information affixed to each reagent cartridge.

What is claimed is:

1. An automatic analyzer, comprising:
a plurality of sample containers disposed at different positions and allocated for different samples to be analyzed;
a rotor capable of carrying a plurality of reagent cartridges each comprising a photometric cuvette, a reagent cuvette in which a reagent is hermetically sealed, and an information exhibiting portion, the information exhibiting portion exhibiting information including an analyte type required as a sample for the reagent, the reagent being necessary for analysis of a sample;
a rotor driving unit for rotating said rotor;
an information reading unit for reading information from said information exhibiting portion of said reagent cartridge;
a probe capable of sucking and discharging a liquid;
a probe drive unit for driving said probe;
an optical measurement unit comprising a light source and a photodetector for performing an absorbance measurement on said photometric cuvette of said reagent cartridge;
a memory unit for storing the information read by said information reading unit; and
a control unit for controlling the individual units of the analyzer, wherein said control unit is configured to reference the information stored in said memory unit, identify the sample container in which a sample required by said reagent cartridge is loaded based on the information, including analyte type required as a sample for the reagent, stored in said memory unit, and control said probe driving unit such that said probe can be positioned in the identified sample container,
wherein said photometric cuvette is moved by the rotation of said rotor on a circle with a second radius that intersects with a circular arc with a first radius at a first point of intersection, and wherein said reagent cuvette is moved by the rotation of said rotor on a circle with a third radius that intersects with said circular arc with said first radius at a second point of intersection, wherein
said control unit controls said rotor driving unit to position said photometric cuvette at said first point of intersection when causing a fluid to be discharged to said photometric cuvette, while controlling said probe driving unit so as to position said probe at said first point of intersection, and wherein
said control unit controls said rotor driving unit to position said first reagent cuvette at said second point of intersection when causing a reagent to be sucked from said reagent cuvette, while controlling said probe driving unit so as to position said probe at said second point of intersection.

2. The automatic analyzer according to claim 1, wherein said reagent cartridge comprises a first reagent cuvette and a second reagent cuvette, wherein
said first reagent cuvette is moved by the rotation of said rotor on said circle with said third radius that intersects with said circular arc with said first radius at said second point of intersection,
said second reagent cuvette is moved by the rotation of said rotor on a circle with a fourth radius that intersects with said circular arc with said first radius at a third point of intersection, and wherein
said control unit controls said rotor driving unit to position said second reagent cuvette at said third point of intersection when causing a reagent to be sucked from said second reagent cuvette, while controlling said probe driving unit so as to position said probe at said third point of intersection.

3. The automatic analyzer according to claim 1, wherein said control unit is configured to detect a change in capacitance between said probe and ground potential.

4. The automatic analyzer according to claim 1, further comprising a washing unit positioned on said circular arc with said first radius for washing said probe.

5. The automatic analyzer according to claim 4, further comprising a cleaning solution container positioned on said circular arc with said first radius for containing a cleaning solution, wherein said probe is adapted to suck said cleaning solution from said cleaning solution container and discharge it in said washing unit.

6. The automatic analyzer according to claim 1, wherein the reagent contained in said reagent cuvette and said sample are injected into said photometric cuvette.

7. The automatic analyzer according to claim 1, wherein said control unit identifies the sample container in which the sample required by a particular reagent cartridge is stored from a plurality of sample containers having different types of samples.

8. The automatic analyzer according to claim 1, wherein said plurality of sample containers contain samples selected from the group consisting of blood serum, blood plasma, whole blood and urine.

9. An automatic analyzer comprising:
a plurality of sample containers disposed at different positions and allocated for different samples to be analyzed;
a rotor capable of carrying a plurality of reagent cartridges each comprising a photometric cuvette, a reagent cuvette in which a reagent is hermetically sealed, and an information exhibiting portion for exhibiting information in the form of a two-dimensional code, the information exhibiting portion exhibiting information including an analyte type required as a sample for the reagent, the reagent being necessary for analysis of a sample;
a rotor driving unit for rotating said rotor;
an information reading unit for reading the information from said information exhibiting portion of said reagent cartridges;
a probe capable of sucking and discharging a fluid;
a probe driving unit for driving said probe;
an optical measurement unit comprising a light source and a photodetector for performing an absorbance measurement on said photometric cuvette of said reagent cartridges;
a memory unit for storing the information read by said information reading unit; and
a control unit for controlling the individual units of the analyzer, wherein said control unit is configured to reference the information stored in said memory unit, identify the sample container in which the sample required by a particular reagent cartridge is stored based on the information, including analyte type required as a sample for the reagent, stored in said memory unit, and control said probe driving unit so as to position said probe in the identified sample container,
wherein said photometric cuvette is moved by the rotation of said rotor on a circle with a second radius that intersects with a circular arc with a first radius at a first point of intersection, and wherein said reagent cuvette is moved by the rotation of said rotor on a circle with a third radius that intersects with said circular arc with said first radius at a second point of intersection, wherein said control unit controls said rotor driving unit to position said photometric cuvette at said first point of intersection when causing a fluid to be discharged to said photometric cuvette, while controlling said probe driving unit so as to position said probe at said first point of intersection, and wherein said control unit controls said rotor driving unit to position said first reagent cuvette at said second point of intersection when causing a reagent to be sucked from said reagent cuvette, while controlling said probe driving unit so as to position said probe at said second point of intersection.

10. The automatic analyzer according to claim 9, wherein the information exhibiting portion further comprises information regarding the required amount of sample, the required amount of reagent, timing for photometry, and a formula for converting absorbance into concentration is stored in said information exhibiting portion.

11. The automatic analyzer according to claim 9, wherein each of said reagent cartridges has a seal attached to the top surface thereof, said seal being color-coded by the type of sample corresponding to each reagent cartridge.

12. The automatic analyzer according to claim 9, wherein said control unit identifies the sample container in which the sample required by a particular reagent cartridge is stored from a plurality of sample containers having different types of samples.

13. The automatic analyzer according to claim 9, wherein said plurality of sample containers contain samples selected from the group consisting of blood serum, blood plasma, whole blood and urine.

* * * * *